(12) United States Patent
Busija

(10) Patent No.: US 6,313,112 B1
(45) Date of Patent: Nov. 6, 2001

(54) METHODS OF PROTECTING NEURONAL FUNCTION

(75) Inventor: David W. Busija, Winston-Salem, NC (US)

(73) Assignee: Wake Forest University, Winston-Salem, NC (US)

(*) Notice: Subject to any disclaimer, the term of this patent is extended or adjusted under 35 U.S.C. 154(b) by 0 days.

(21) Appl. No.: 09/694,121

(22) Filed: Oct. 20, 2000

Related U.S. Application Data

(60) Provisional application No. 60/160,976, filed on Oct. 22, 1999.

(51) Int. Cl.$^7$ .................................................... A61K 31/54
(52) U.S. Cl. ....................................... 514/223.2; 514/223.5
(58) Field of Search ................................ 514/223.2, 223.5

(56) References Cited

U.S. PATENT DOCUMENTS

| 5,281,599 | * | 1/1994 | Murphy et al. | 514/305 |
| 5,451,580 | * | 9/1995 | Murphy et al. | 514/212 |
| 6,031,089 | * | 2/2000 | Bienkowski | 536/23.5 |

OTHER PUBLICATIONS

Abercrombie, M. Estimation of Nuclear Population from Microtome Sections. *Anatomical Record*. 1946;94:239–247.
Armstead, W.M. et al. Postischemic Generation of Superoxide Anion by Newbron Pig Brain. *Am J. Physiol*. 1988;255:H401–3.
Auchampach, J. et al. Blockade of Ischemic Preconditioning in Dogs by the Novel ATP–Dependent Potassium Channel Antagonist Sodium 5–Hydroxydecanoate. *Cardiovasc. Res*. 1992;26:1054–62.
Baines, C.P. et al. Ischemic Preconditioning Depends on Interaction between Mitochondrial KAPT Channels and Actin Cytoskeleton. *Am J Physiol*. 1999;276:H1361–68.
Bari, F. et al. Kainite–Induced Cerebrovascular Dilation Is Resistant to Ischemia in Piglets. *Stroke*. 1997;28:1272–6.
Bari, F. et al. Differential Effects of Short–Term Hypoxiaand Hypercapnia on N–Methyl–D–Aspartate–Induced Cerebral Vasodilation in Piglets. *Stroke*. 1996;271634–39.
Beasley, T.C. et al. Cerebral Ischemia/Reperfusion Increases Endothelial Nitric Oxide Synthase Levels by an Indomethacin–Sensitive Mechanism. *J Cereb Blood Flow Metab*. 1998;18:88–86.
Busija, D.W. et al. Effects of Ischemia on Cerebrovascular Responses to N–Methyl–D–Aspartate in Piglets. *Am J Physiol*. 1996;270:H1225–30.
Busija, D.W. et al. Dilator Effects of Amino Acid Neurotransmitters on Piglet Pial Arterioles. *Am J Physiol*. 1989;257:H1200–3.
Dugan, L.L. et al. Mitochondrial Production of Reactive Oxygen Species in Cortical Neurons following Exposure to N–Methyl–D–Aspartate. *J Neurosci*. 1995;15:6377–88.

Dykens, J.A. et al. Isolated Cerebral and Cerebellar Mitochondria Produce Free Radicals When Exposed to Elevated $Ca^{2+}$ and $Na^+$: Implications for Neurodegeneration. *J Neurochem*. 1994;63:584–91.
Faraci, F.M. et al. Nitric Oxide Mediates Vasodilation in Response to Activation of N–Methyl–D–Aspartate Receptors in Brain. *Circ Res*. 1993;72:476–80.
Gardia De Arriba, S. et al. Neuroprotection by ATP–Dependent Potassium Channels in Rat Neocortical Brain Slices during Hypoxia. *Neuroscience Letters* 273:13–16 (1999).
Garlid, K.D. et al. Cardioprotective Effect of Diazoxide and Its Interaction with Mitochondrial ATP–Sensitive $K^+$ Channels: Possible Mechanism of Cardioprotection. *Circ Res*. 1997;81:1072–82.
Garlid, K.D. et al. Cation Transport in Mitochondria. *Biochem Biophys Acta*. 1996;1275:123–6.
Garlid K.D. et al. The Mitochrondial KATP Channel as a Receptor for Potassium Channel Openers. *J Biol Chem,,* 1996;271:8796–99.
Gross, G.J, et al. Sarcolemmal Versus Mitochondrial ATP–Sensitive $K^+$Channels and Myocardial Preconditioning. *Circ Res*1999;973–79.
Gross, G. et al.Blockade in the ATP–Sensitive Potassium Channels Prevents Myocardial Preconditioning in Dogs. *Circ Res*. 1992;70:223–33.
Gunter, T.E. et al. Mitochondrial Calcium Transport: Physiological and Pathological Relevance. *Am J Physiol*. 1994;267:C313–39.
Halestrap, A.P. Regulation of Mitochondrial Metabolism through Changes in Matrix Volume. *Biochem Soc Trans*. 1994;22:522–9.
Hoffman, D.J. et al., Hypoxia–Induced Modification of the N–Methyl–D–Aspartate Receptorin the Brain of the Newborn Piglet. *Neurosci Lett*. 1994;167:156–160.
Holmuhamedov, E.L. et al. Mitochondrial ATP–Sensitive $K^+$ Channels Modulate Cardiac Mitochondrial Function. *Am J Physiol*. 1998;275:H1567–76.

(List continued on next page.)

Primary Examiner—Raymond Henley, III
(74) Attorney, Agent, or Firm—Charles W. Chalkins; Pat Winston Kennedy; Kilpatrick Stockton LLP

(57) ABSTRACT

The present invention is generally directed to potassium adenosine triphosphate ("$K_{ATP}$") channel opening compositions. The present invention also relates to the use of $K_{ATP}$ channel openers in therapeutic applications. The $K_{ATP}$ channel opening compositions of the present invention include diazoxide (7-chloro-3-methyl-2H-1,2,4-benzo-thiadiazine 1,1-dioxide) and aprikalim. According to the present invention, diazoxide and aprikalim can be used independently, or in combination. The present also relates to therapeutic methods for protecting neuronal function utilizing $K_{ATP}$ channel openers. Methods of the present invention may be advantageous for protecting neuronal function, prior to medical procedures, after stroke-like events or other events associated with reductions in blood flow, and/or for preserving tissues or organs against cellular injury and death during removal, storage, transplantation or reattachment.

28 Claims, 4 Drawing Sheets

OTHER PUBLICATIONS

Inoue, I. et al. ATP–Sensitive K$^+$ Channel in the Mitochondrial Inner Membrane. *Nature*. 1991;352:244–47.

Liu, Y. et al. Mitochondrial ATP–Dependent Potassium Channels: Novel Effectors of Cardioprotection? *Circulation*. 1998;97:2463–9.

Mehta, V. et al. Enhancement of Graft Survival and Sensorimotor Behavioral Recovery in Rats undergoing Transplantation with Dopaminergic Cells Exposed to Glial Cell Line—Derived Neurotrophic Factor. *Journal of Neurosurgery*. 1998;88:1088–1095.

Meng, W. et al. Glutamate–Induced Cerebral Vasodilation Is Mediated by Nitric Oxide through N–Methyl-$_D$–Aspartate Receptors. *Stroke*. 1995;26:857–62.

Nikkaj, G. et al. A Micro Transplantation Approach for Cell Suspension Grafting in the Rat Parkinson Model: a Detailed Account of the Methodology. *Neuroscience*. 1994;63:57–72.

Nikkah, G. et al. Preservatation of Fetal Ventral Mesencephalic Cells by Cool Storage: In vitro Viability and TH–Positive Neuron Survival after Micro Transplantatin to the Striatum. *Brain Research*. 1990;687:22–34.

Paucek, P. et al. Inhibition of the Mitochondrial K$_{ATP}$ Channel by Long Chain Acyl–CoA Esters and Activationby Guanine Nucleotides. *J Biol Chem.*. 1996;271:32084–8.

Pourcyrous, M. et al. Brain Superoxide Anion Generation in Asphyxiated Piglets and the Effect of Indomethacin at Therapeutic Dose. *Pediatr Res*. 1993;34:366–369.

Rechncrona, S. et al. Recovery of Brain Mitochondrial Function in the Rat after Complete and Incomplete Cerebral Ischemia. *Stroke*. 1979;10:437–46.

Sato, T. et al. Modulation of Mitochondrial ATP–Dependent K$^+$ Channels by Protein Kinase C. *Circ Res*. 1998;83:110–4.

Schulz, et al. Involvemet of Activation of ATP–Dependent Potassium Channels in Ischemic Preconditioning in Swine. *Am J Physiol*. 1994;267:H1341–52.

Sims, N.R. Selective Impairment of Respiration in Mitochondria Isolated from Brain Subregions following Transient Forebrain Ischemia in the Rat. *J Neurochem*. 1991;56;1836–44.

Szewczyk, A. et al. ATP–Regulated K$^+$ Channel in Mitochondria: Pharmacology and Function. *J Bioenerg Biomembr*. 1996;28:147–52.

Veltkamp R. et al. Inhibitors of Protein Synthesis Preserver the N–Methyl-$_D$–Aspartate–Induced Cerebral Arteriolar Dilation after Ischemia in Piglets. *Stroke*. 1999;30:148–52.

Veltkamp R. et al. Potassium Channel Activators Protect the N–Methyl–Asparatate–Induced Cerebral Vascular Dilation after Combined Hypoxia and Ischemia in Piglets. *Stroke*. 1998;29:837–43.

\* cited by examiner

METHODS OF PROTECTING NEURONAL FUNCTION

STATEMENT OF RELATED APPLICATIONS

The present application claims priority under 35 USC §119 from U.S. provisional patent application serial number 60/160,976, filed Oct. 22, 1999, the disclosure of which is hereby incorporated herein by reference.

STATEMENT REGARDING FEDERALLY SPONSORED RESEARCH

This invention was made with US government support from a grant funded by the National Institutes of Health HL-30260, HL-46558, and HL-50587. The US government may have certain rights in the invention.

FIELD OF THE INVENTION

The present invention generally relates to potassium adenosine triphosphate ("$K_{ATP}$") channel openers and their use. According to the present invention, diazoxide (7-chloro-3-methyl-2H-1,2,4-benzo-thiadiazine 1,1-dioxide) or aprikalim, or the combination, may be utilized as a selective $K_{ATP}$ channel opener for neuronal channels. The present also relates to therapeutic methods for protecting neuronal function utilizing $K_{ATP}$ channel openers. Methods of the present invention may be advantageous for protecting neuronal function, prior to medical procedure, after stroke-like events or other events associated with reductions in blood flow, and/or for preserving tissues or organs against cellular injury and death during removal, storage, transplantation or reattachment.

BACKGROUND

Strokes and other events associated with reductions in blood flow to the brain continue to result in serious and costly neurological sequelae such as: 1) loss of normal neurological function such as movement or memory; 2) altered neurological function (i.e., seizure type activity); and/or 3) death of the affected individual. Examples of disruptions in the cerebral blood flow include, but are not limited to, cardiac failure, hypotensive shock, occlusion of carotid arteries for endarterectomy, occlusion of cerebral arteries for aneurysm surgery, and lodging of microvascular emboli during cardiopulmonary bypass. Further, such events account for considerable costs to society in terms of the medical care and loss of productivity.

A number of putative neuroprotective agents have been developed over the last several decades, but the results of these agents in clinical trials and practice have been disappointing at best. For example, non-selective stimulators of potassium channels such as aprikalim and NS1619 have been shown to protect the brain under a wide range of ischemic conditions. However, two basic limitations typically occur with these compounds. First, these potassium channel stimulators are not selective for cellular localization, so that it is impossible to determine the situs of their function. This is important because the effects of these agents at locations distinct from mitochondria may counteract or interfere with protective functions. Second, mechanisms of action for these non-selective stimulators have yet to be determined, and thus results have been difficult to interpret. There, thus, remains a need to develop neuroprotective agents that can improve neuronal cell function and recovery and prevent cell death after stroke-like events or events associated with reductions of cerebral blood flow (ischemia).

SUMMARY OF THE INVENTION

The present invention is generally directed to potassium adenosine triphosphate ("$K_{ATP}$") channel opening compositions. The present invention also relates to the use of $K_{ATP}$ channel openers in therapeutic applications.

The $K_{ATP}$ channel opening compositions of the present invention include diazoxide (7-chloro-3-methyl-2H-1,2,4-benzo-thiadiazine 1,1-dioxide) and aprikalim. According to the present invention, diazoxide and aprikalim can be used independently, or in combination.

In methods of the present invention, diazoxide may be utilized as a selective $K_{ATP}$ channel opener, particularly in neuronal channels and/or mitochondria. The present invention includes therapeutic applications of diazoxide as a neuroprotective agent. Alternate methods and therapeutic methods of the present invention comprise the use of aprikalim, a $K_{ATP}$ channel opener with vasodilation.

In a first aspect the present invention relates to a therapeutic application of a $K_{ATP}$ channel opener to provide protection to an individual's brain against neurological events. Examples of neurological events include, but are not limited to, stroke, reduction of cerebral blood flow (ischemia); events resulting from trauma, for example trauma to the head; and/or similar events that are generally an initial and unplanned event.

In another aspect the present invention relates to a therapeutic application of $K_{ATP}$ channel opener to provide protection to an individual's brain prior to scheduled, or unscheduled, procedures that may affect the cerebral circulation and brain. In general, the methods of the present invention may be utilized with any medical procedure that may affect neuronal function. Examples of procedures include, but are not limited to, surgical procedures, for example endarterectomy or cardiopulmonary bypass; cardiac catherization; angioplasty; and other medical procedures that may affect cerebral circulation. A procedure may also comprise the administration of pharmaceutical compositions that may affect cerebral circulation.

In a further aspect, the present invention relates to a therapeutic application of a $K_{ATP}$ channel opener to provide protection to tissues and organs against cellular damage associated with transplantation and reattachment procedures.

The $K_{ATP}$ channel opener may comprise diazoxide, or may comprise aprikalim, or may comprise a combination of diazoxide and aprikalim.

In a still further aspect, the present invention relates to the use of diazoxide as a selective mitochondrial $K_{ATP}$ channel opener.

Diazoxide is a selective stimulator of ATP-sensitive potassium channels in mitochondria, and provides several advantages over non-selective stimulators of potassium channels. The methods of the present invention may be utilized to target the mitochondria to preserve function of the cellular components and to improve the survival of the affected cells. By targeting a specific mechanism, it is possible to minimize unwanted effects that could interfere with cellular protection. In contrast to non-selective potassium channel stimulators, which by their mode of action increase general blood flow to various cellular locations, diazoxide may be utilized to protect mitochondria without substantial effects on blood flow or blood vessel responsiveness.

In a therapeutic method of the present invention, a $K_{ATP}$ channel opener is administered in a therapeutically effective dosage to mammals in need of such treatment. The term "therapeutically effective dosage" as used in the present invention is defined as the dosage which provides effective protection or preservation of neuronal function for mammals, in particular humans, for the medical conditions described herein. As described in detail below, in general, a therapeutically effective dosage in a method of the present invention may comprise a dosage ranging between approximately, 0.1 $\mu$M to 150 $\mu$M, preferably 0.5 $\mu$M to 100 $\mu$M, more preferably, 1 $\mu$M to 50 $\mu$M, and still more preferably 1 $\mu$M to about 10 $\mu$M. It is further contemplated that the therapeutic applications for $K_{ATP}$ channel openers described herein are by no means limited to the disclosed medical conditions, but instead include other conditions that will be apparent to those skilled in the art.

In an embodiment of the present invention, diazoxide, or a mammalian metabolic conjugate thereof, is administered to the brain at varying dosages ranging between approximately, 0.1 $\mu$M to 150 $\mu$M, preferably 0.5 $\mu$M to 100 $\mu$M, more preferably, 1 $\mu$M to 50 $\mu$M, and still more preferably 1 $\mu$M to about 10 $\mu$M. The diazoxide may be administered into a mammals circulatory system or into a mammal's brain ventriculocistemal (fluid circulation) system prior to planned, or unplanned, surgical procedures that may affect the cerebral circulation and brain.

Alternatively, diazoxide may be administered into a mammal's circulatory system or into the brain following a neurological event such as stroke or general circulatory failure in order to protect the brain against reperfusion injury or to prevent damage during secondary insults.

Further, neuroprotective $K_{ATP}$ channel opener agents like diazoxide may be administered to a mammal, for example through the circulatory system, immediately prior to the removal of tissue or organs in order to protect the tissues during removal, transport, and then subsequent transplantation or reattachment.

In additional embodiments of the present invention, a therapeutic method may comprise administering a therapeutically effective amount of aprikalim, or a mammalian metabolic conjugate thereof, in the applications discussed herein. In additional embodiments of the present invention, a therapeutic method may comprise administering a therapeutically effective amount of diazoxide and a therapeutically effective amount of aprikalim in the applications discussed herein. Generally a therapeutically effective amount of aprikalim will comprise a dosage ranging between approximately, 0.1 $\mu$M to 150 $\mu$M, preferably 0.5 $\mu$M to 100 $\mu$M, more preferably, 1 $\mu$M to 50 $\mu$M, and still more preferably 1 $\mu$M to about 10 $\mu$M.

As will be understood by those of ordinary skill in the art, mammalian metabolic conjugates of diazoxide and/or aprikalim are included within the definition of diazoxide and aprikalim as used in the descriptions of methods of the present invention.

The preceding and further objects of the present invention will be appreciated by those of ordinary skill in the art from a reading of the detailed description of the preferred embodiments which follow, such description being merely illustrative of the present invention.

DETAILED DESCRIPTION OF THE INVENTION

Figure 1:
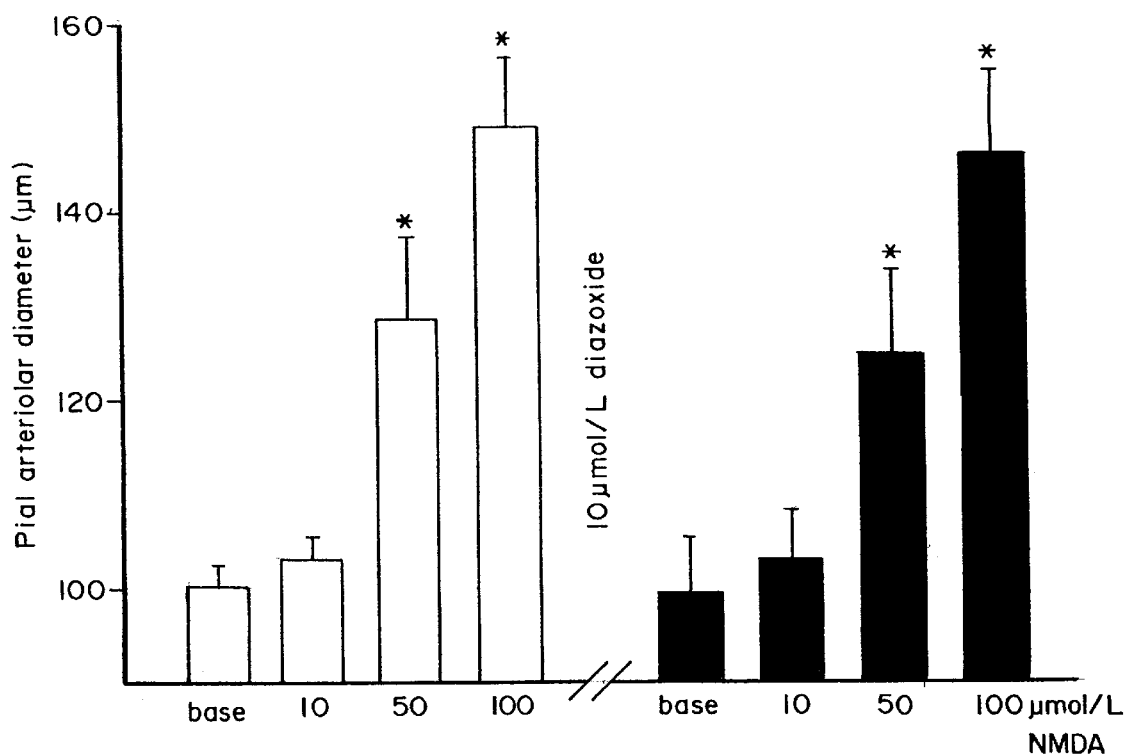
FIG. 1 illustrates the effects of 10 $\mu$mol/L diazoxide on pial arteriolar responses to N-methyl-D-aspartate (NMDA). NMDA induced dose-dependent vasodilation that was unaffected 1 hour after topical application of diazoxide for 10 minutes (n=4). base: baseline diameter; *significantly different from corresponding baseline values, p<0.05.

As described above, the present invention comprises potassium adenosine triphosphate ("$K_{ATP}$") channel openers and methods for their use. The $K_{ATP}$ channel openers of the present invention include diazoxide (7-chloro-3-methyl-2H-1,2,4-benzo-thiadiazine 1,1-dioxide) and aprikalim.

The present invention includes therapeutic applications of a $K_{ATP}$ channel opener as a neuroprotective agent. Embodiments of the present invention include therapeutic applications of a $K_{ATP}$ channel opener neuroprotective agent to protect neuronal function prior to surgical procedures that may affect the cerebral circulation and brain as well as subsequent to a neurological event. Additional embodiments of the present invention are further directed to the use of $K_{ATP}$ channel opener to preserve tissues and organs during removal, transport, transplantation, and reattachment procedures, and to protect the tissues and organs against cellular injury and death during such procedures.

In embodiments of the present invention a $K_{ATP}$ channel opener or a mammalian conjugate thereof is administered in a therapeutically effective dosage into the circulation or into the brain ventriculocistemal (fluid circulation) system prior to a procedure that may affect the brain and cerebral circulation. For example, cardiopulmonary bypass procedures are typically scheduled several days or weeks prior to the surgery. One complication of the bypass is the formation of microemboli that lodge within the cerebral blood vessels, resulting in local areas of blood flow cessation or ischemia. Ischemia is caused by an increase in the fluid pressure within the skull and a cessation of the cerebral blood flow. The presence of microemboli may account for the high proportion of neurological problems seen in these patients. In accordance with methods of the present invention, stimulation of ATP-activated potassium channels prior to the bypass procedure can protect the neurons in areas of high microemboli density and reduce the likelihood of neurological problems. A $K_{ATP}$ channel opener may be used with other planned surgical procedures where microemboli are released into the brain circulation or transient disruption of blood flow to the brain occurs including, but not limited to, carotid endarterectomy, clipping of aneurysms, etc.

In another method of the present invention, a $K_{ATP}$ channel opener is administered in a therapeutically effective dosage into the circulation or into the brain ventriculocistemal (fluid circulation) system of a mammal following a neurological event, for example an unexpected neurological event, such as stroke or general circulatory failure. A $K_{ATP}$ channel opener protects the brain against reperfusion injury, and prevents damage during secondary insults. For example, thrombolysis after stroke results in restoration of blood flow to the affected stroke area. Neurological damage occurs due to reintroduction of oxygen to the affected tissue. Additionally, following heart attacks in adults or asphyxia in babies, arterial blood pressure is insufficient to push blood flow through the brain's blood vessels. During restoration of the arterial blood pressure and brain blood flow, the reintroduction of oxygen results in the production of harmful substances that damage the neurons. Particularly in the neonate, resuscitation of babies following asphyxia often results in delayed (3–24 hours) neurological sequelae such as seizure activity, secondary bouts of apnea, and intracranial bleeding. Anticipation of these secondary insults and administration of diazoxide could limit the total neurological impairment.

In another method of the present invention, a $K_{ATP}$ channel opener is administered in a therapeutically effective dosage into the circulation immediately prior to the removal of tissue or organs from a mammal, in particular humans, in order to protect the tissues and organs during removal, transport, transplantation and/or reattachment. With this approach, circulatory effects are minimized while protection is maximized.

As set forth above, diazoxide and aprikalim are suitable $K_{ATP}$ channel opener composition for use in methods of the present invention.

As utilized herein, a therapeutically effective dosage refers to an amount sufficient to provide effective protection or preservation of neuronal function for mammals, in particular humans, for the medical conditions described herein. In embodiments of the present invention, diazoxide may be administered at varying dosages ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M.

In alternate embodiments of the present invention, an effective dosage may refer to an amount of diazoxide sufficient to have $K_{ATP}$ channel activity. Generally effective dosages for this activity will be similar to the therapeutically effective dosages referred to above.

In embodiments of the present invention utilizing aprikalim as a $K_{ATP}$ channel opener, effective dosages of aprikalim include dosage amounts ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M.

In alternative embodiments of the present invention, diazoxide is administered in combination with aprikalim in a combined amount sufficient to be therapeutically effective. In general dosage amounts ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M, aprikalim may be administered in combination with diazoxide.

The present invention also includes methods for the use of diazoxide (7-chloro-3-methyl-2H-1,2,4-benzo-thiadiazine 1,1-dioxide) as a potassium adenosine triphosphate ("$K_{ATP}$") channel opener, particularly as a selective $K_{ATP}$ channel opener in neuronal channels and/or mitochondria. The present invention includes therapeutic applications of diazoxide as a neuroprotective agent. The methods and therapeutic methods of the present invention may further comprise the use of aprikalim, a $K_{ATP}$ channel opener with vasodilation.

Additional embodiments of the present invention are directed to therapeutic applications of a neuroprotective agent, diazoxide, to protect neuronal function prior to surgical procedures that may affect the cerebral circulation and brain as well as subsequent to a neurological event. Further embodiments are directed to the use of diazoxide to preserve tissues and organs during removal, transport, transplantation, and reattachment procedures, and to protect the tissues and organs against cellular injury and death during such procedures.

As also described above, in these embodiments of the present invention diazoxide or a mammalian conjugate thereof is administered in a therapeutically effective dosage into the circulation or into the brain ventriculocistemal (fluid circulation) system prior to a procedure that may affect the brain and cerebral circulation. For example, cardiopulmonary bypass procedures are typically scheduled several days or weeks prior to the surgery. One complication of the bypass is the formation of microemboli that lodge within the cerebral blood vessels, resulting in local areas of blood flow cessation or ischemia. Ischemia is caused by an increase in the fluid pressure within the skull and a cessation of the cerebral blood flow. The presence of microemboli may account for the high proportion of neurological problems seen in these patients. In accordance with methods of the present invention, stimulation of ATP-activated potassium channels prior to the bypass procedure can protect the neurons in areas of high microemboli density and reduce the likelihood of neurological problems. Diazoxide may be used with other surgical procedures where microemboli are released into the brain circulation or transient disruption of blood flow to the brain occurs including, but not limited to, carotid endarterectomy, clipping of aneurysms, etc.

In another method of the present invention, diazoxide is administered in a therapeutically effective dosage into the circulation or into the brain ventriculocistemal (fluid circulation) system of a mammal following an neurological event, for example an initial unplanned neurological event, such as stroke or general circulatory failure. Diazoxide protects the brain against reperfusion injury, and prevents damage during secondary insults. For example, thrombolysis after stroke results in restoration of blood flow to the affected stroke area. Neurological damage occurs due to reintroduction of oxygen to the affected tissue. Additionally, following heart attacks in adults or asphyxia in babies, arterial blood pressure is insufficient to push blood flow through the brain's blood vessels. During restoration of the arterial blood pressure and brain blood flow, the reintroduction of oxygen results in the production of harmful substances that damage the neurons. Particularly in the neonate, resuscitation of babies following asphyxia often results in delayed (3–24 hours) neurological sequelae such as seizure activity, secondary bouts of apnea, and intracranial bleeding. Anticipation of these secondary insults and administration of diazoxide could limit the total neurological impairment.

In another method of the present invention, diazoxide is administered in a therapeutically effective dosage into the circulation prior to the removal of tissue or organs from a mammal, in particular humans, in order to protect the tissues and organs during removal, transport, transplantation and/or reattachment. With this approach, circulatory effects are minimized while protection is maximized.

As utilized herein, a therapeutically effective dosage refers to an amount sufficient to provide effective protection or preservation of neuronal function for mammals, in particular humans, for the medical conditions described herein. In embodiments of the present invention, diazoxide is administered at varying dosages ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M.

In alternate embodiments of the present invention, an effective dosage may refer to an amount of diazoxide sufficient to have $K_{ATP}$ channel activity. Generally effective dosages for this activity will be similar to the therapeutically effective dosages referred to above.

Embodiments of the present invention also include the administration of aprikalim, in a dosage amounts ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M, in place of diazoxide in the methods described in the foregoing paragraphs.

In other embodiments of the present invention, diazoxide is administered in combination with aprikalim in a combined amount sufficient to be therapeutically effective. In general dosage amounts ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M, aprikalim may be administered in combination with diazoxide.

Specific embodiments of the methods of the present invention, include, but are not limited to the following.

A method for activating neuronal $K_{ATP}$ channels comprising delivering a sufficient amount of a $K_{ATP}$ channel opening composition to a channel site. Suitable $K_{ATP}$ channel opening compositions comprise diazoxide (7-chloro-3-methyl-2H-1,2,4-benzo-thiadiazine 1,1-dioxide), aprikalim and combinations thereof. A sufficient amount may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. The method may further comprise selective activation of $K_{ATP}$ channels. In an alternate embodiment, a method for activating neuronal $K_{ATP}$ channels comprises delivering a sufficient amount of diazoxide and aprikalim to a channel site. The amount of aprikalim may be the same or different than the amount of diazoxide. A sufficient amount of aprikalim may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. The step of delivering may comprise introducing the dosage of the $K_{ATP}$ channel opening composition into a mammals circulatory system, ventriculocistemal system and/or other mammalian fluid system. Diazoxide includes any derivative, analog, or metabolite thereof having similar functionality. Similarly, aprikalim includes any derivative, analog or metabolite thereof having similar functionality.

A method for activating mitochondrial $K_{ATP}$ channels comprising delivering a sufficient amount of diazoxide (7-chloro-3-methyl-2H-1,2,4-benzo-thiadiazine 1,1-dioxide) to a mitochondrial site. A sufficient amount may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. The method may further comprise selective activation of $K_{ATP}$ channels. In an alternate embodiment, a method for activating mitochondrial $K_{ATP}$ channels comprises delivering a sufficient amount of diazoxide and aprikalim to a mitochondrial site. The amount of aprikalim may be the same or different than the amount of diazoxide. A sufficient amount of aprikalim may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. The step of delivering may comprise introducing the dosage of diazoxide or diazoxide and aprikalim into a mammals circulatory system, ventriculocistemal system and/or other mammalian fluid system. Diazoxide includes any derivative, analog, or metabolite thereof having similar functionality. Similarly, aprikalim includes any derivative, analog or metabolite thereof having similar functionality.

A method of protecting neuronal function in vivo in the brain and the cerebral circulation, comprising the step of administering to a mammal a therapeutically effective dosage of a $K_{ATP}$ channel opening composition prior to a medical or surgical procedure. The medical or surgical procedures include, but are not limited to, cardiopulmonary bypass, carotid endarterectomy, clipping of aneurysms, cardiac catherization, angioplasty and the like. Suitable $K_{ATP}$ channel opening compositions comprise diazoxide (7-chloro-3-methyl-2H-1,2,4-benzo-thiadiazine 1,1-dioxide), aprikalim and combinations thereof. A therapeutically effective amount may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. In an alternate embodiment, a method for method of protecting neuronal function in vivo comprises administering to a mammal a therapeutically effective amount of diazoxide and aprikalim prior to a medical or surgical procedure. The amount of aprikalim may be the same or different than the amount of diazoxide. A sufficient amount of aprikalim may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. Diazoxide includes any derivative, analog, or metabolite thereof having similar functionality. Similarly, aprikalim includes any derivative, analog, or metabolite thereof having similar functionality.

A method of protecting neuronal function in vivo in the brain and the cerebral circulation, comprising the step of administering to a mammal a therapeutically effective dosage of a $K_{ATP}$ channel opening composition immediately following a neurological event, for example an unscheduled neurological event. Immediately may comprise, within 1 hour, preferably within minutes, more preferably within 10 minutes, even more preferably within 5 minutes and still more preferably within 1 minute after the neurological event. The neurological event includes stroke, general circulatory failure, seizures, apnea, and intracranial bleeding. Suitable $K_{ATP}$ channel opening compositions comprise diazoxide (7-chloro-3-methyl-2H-1,2,4-benzo-thiadiazine 1,1-dioxide), aprikalim and combinations thereof. A therapeutically effective amount may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. In an alternate embodiment, a method for method of protecting neuronal function in vivo comprises administering to a mammal a therapeutically effective amount of diazoxide and aprikalim. The amount of aprikalim may be the same or different than the amount of diazoxide. A sufficient amount of aprikalim may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. Diazoxide includes any derivative, analog, or metabolite thereof having similar functionality. Similarly, aprikalim includes any derivative, analog, or metabolite thereof having similar functionality.

A method of protecting tissues and organs against cellular damage associated with transplantation or reattachment, comprising the step of infusing a therapeutic dosage of a $K_{ATP}$ channel opening composition into tissues or organs prior to the removal of the tissues or organs from a mammal. The method may further comprise the step of removing the infused tissues or organs from the mammal and then transplanting the tissues and organs into another mammal. Suitable $K_{ATP}$ channel opening compositions comprise diazoxide (7-chloro-3-methyl-2H-1,2,4-benzo-thiadiazine 1,1-dioxide), aprikalim and combinations thereof. A therapeutic dosage may comprise a dosage ranging between approximately ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. In an alternate embodiment, a method for protecting tissues and organs neuronal function in vivo comprises infusing into the tissue or organ a therapeutically effective amount of diazoxide and aprikalim. The amount of aprikalim may be the same or different than the amount of diazoxide. A sufficient amount of aprikalim may comprise a dosage ranging between approximately 0.1 $\mu$M to 150 $\mu$M, preferably 0.5 $\mu$M to 100 $\mu$M, more preferably, 1 $\mu$M to 50 $\mu$M, more preferably 1 $\mu$M to about 10 $\mu$M, further preferably 2–8 $\mu$M, more preferably 3–7 $\mu$M. Diazoxide includes any derivative, analog, or metabolite thereof having similar functionality. Similarly, aprikalim includes any derivative, analog, or metabolite thereof having similar functionality.

The features and advantages of the present invention are illustrated by the following Examples. In the following examples, neuronal cell function was assessed by examining cerebral arteriolar responses to the neurotransmitter, NMDA. NMDA elicits neuronally mediated cerebral arteriolar vasodilation that is reduced by ischemia/reperfusion. This sequence has been preserved by pretreatment with the ATP-sensitive potassium channel opener, aprikalim, although the mechanism is uncertain. In the heart, mitochondrial ATP-sensitive potassium channels are involved in the ischemic preconditioning-like effect of potassium channel openers (KCO).

Pial arteriolar diameters were determined using closed crucial window/intravital microscopy in anesthetized piglets. Vascular responses to NMDA were assessed before and 1 hour after 10 minutes of global cerebral ischemia induced by raising intracranial pressure. Subgroups received one of the following pretreatments before ischemia/reperfusion: vehicle; 1–10 $\mu$mol/L diazoxide; and coapplication of 100 $\mu$mol/L 5-hydroxydecanoic acid (5-HD), an ATP-sensitive potassium channel antagonist with diazoxide.

Results demonstrated that NMDA-induced dose-dependent pial arteriolar dilation was not affected by diazoxide treatment only, but was severely attenuated by ischemia/reperfusion. In contrast, diazoxide dose-dependently preserved the NMDA vascular response after ischemia/reperfusion: 10 $\mu$mol/L diazoxide, arteriolar responses were unaltered by ischemia/reperfusion. The effect of diazoxide was antagonized by coapplication of 5-HD with diazoxide. Percent preservation of 100 $\mu$mol/L NMDA-induced vasodilation after ischemia/reperfusion was 53±19% (mean±SEM, n=8) in vehicle-treated controls, as compared to 55±10%, 85±5%, and 99±15% in 1, 5, and 10 $\mu$mol/L diazoxide pretreated animals (n=8,8, and 12, respectively), and 60±15% in the 5-HD+diazoxide pretreated group (n=5).

In view of the foregoing results, mitochondrial ATP-sensitive potassium channel opener, diazoxide, in vivo preserves neuronal function following ischemia/reperfusion as shown by the pial arteriolar responses to NMDA in a dose-dependent manner. Thus, activation of mitochondrial ATP-sensitive potassium channels may play a role in mediating the protective effect of other potassium channel openers.

Glutamate elicits cerebral arteriolar vasodilation in piglets via a multi-step process, which involves activation of neuronal NMDA receptors, stimulation of nitric oxide production by neuronal nitric oxide synthase, and actions of nitric oxide on vascular smooth muscle cells [Busija D W, Leffler C W. Dilator effects of aminuteso acid neurotransmitters on piglet pial arterioles. Am J Physiol. 1989;257:H1200–3; Meng W, Tobin J R, Busija D W. Glutamate-induced cerebral vasodilation is mediated by nitric oxide through N-methyl-D-aspartate receptors. Stroke. 1995;26:857–62; and Faraci F M, Breese K R. Nitric oxide mediates vasodilatation in response to activation of N-methyl-D-aspartate receptors in brain. Circ Res. 1993;72:476–80]. This sequence of events may represent an important mechanism, coupling local blood flow to metabolism and neuronal activity.

NMDA-induced vasodilation is attenuated by hypoxia and ischemia/reperfusion in a dose- and time-dependent manner [Bari F, Errico R A, Louis T M, Busija D W. Differential effects of short-term hypoxia and hypercapnia on N-methyl-D-aspartate-induced cerebral vasodilatation in piglets. *Stroke*. 1996;271634–39; Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30; and Veltkamp R, Domoki F, Bari F, Busija D W. Potassium channel activators protect the N-methyl-D-aspartate-induced cerebral vascular dilation after combined hypoxia and ischemia in piglets. *Stroke*. 1998;29:837–43]. For example, 10 minutes of global ischemia followed by reperfusion reduces NMDA-induced vasodilation by approximately 50%. However, arteriolar dilator responses to exogenously applied nitric oxide are intact [Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30 and Veltkamp R, Domoki F, Bari F, Busija D W. Potassium channel activators protect the N-methyl-D-aspartate-induced cerebral vascular dilation after combined hypoxia and ischemia in piglets. *Stroke*. 1998;29:837–43], thereby implying that the attenuation of the vascular response to NMDA is due to effects of ischemia at the level of the neurons. Further, previous studies indicate that dysfunction of the NMDA receptor rather than general neuronal injury is the primary reason for attenuated arteriolar responsiveness to NMDA [Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30 and Hoffman D J, McGowan J E, Marro P J, Mishoura O P, Delivoria-Papadopoulos M. Hypoxia-induced modification of the N-methyl-D-aspartate receptor in the brain of the newborn piglet. *Neurosci Lett*. 1994;167:156–160]. Although mechanisms involved in attenuated arteriolar dilation to NMDA have yet to be fully elucidated, it appears from the present studies that actions of reactive oxygen species such as superoxide anion are involved. Thus, pharmacological agents that prevent production of superoxide anion or that scavenge this radical prevent attenuation of NMDA-induced dilator responses [Bari F, Errico R A, Louis T M, Busija D W. Differential effects of short-term hypoxia and hypercapnia on N-methyl-D-aspartate-induced cerebral vasodilatation in piglets *Stroke*. 1996;271634–39; Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30; and Pourcyrous M, Leffler C W, Bada H S, Korones S B, Busija D W. Brain superoxide anion generation in asphyxiated piglets and the effect of indomethacin at therapeutic dose. *Pediatr Res*. 1993;34:366–369].

NMDA-induced vasodilation has been utilized by the inventor as a sensitive bioassay to assess the functional integrity of the neuronal-vascular axis. For instance, we have shown that activation of ATP-sensitive potassium channels ($K_{ATP}$) with aprikalim for a brief period immediately prior to combined hypoxic/ischemic stress preserves pial arteriolar dilation to NMDA [Veltkamp R, Domoki F, Bari F, Busija D W. Potassium channel activators protect the N-methyl-D-aspartate-induced cerebral vascular dilation after combined hypoxia and ischemia in piglets. *Stroke*. 1998;29:837–43]. Possible mechanisms of action of $K_{ATP}$ activation could be via hyperpolarization of neurons through plasmolemmal $K_{ATP}$ that may result in (1) reduced glutamate release and (2) smaller increases in intracellular $Ca^{2+}$ levels during ischemia, or perhaps (3) less reactive oxygen species productions during reperfusion. However, intracellular sites of action of potassium channel activators have not been previously considered.

Mitochondrial ATP-sensitive potassium channels have been found in the inner membrane of mitochondria [Inoue I, Nagase H, Kishi K, Higuti T. ATP-sensitive $K^+$ channel in the mitochondrial inner membrane. *Nature*. 1991;352:244–47], and represent a pharmacologically distinct population of ATP-sensitive potassium channels [Garlid K D, Paucek P, Yarov-Yarovoy V, Xiaocheng Sun, Schindler P A. The mitochondrial $K_{ATP}$ channel as a receptor for potassium channel openers. *J Biol Chem*. 1996;271:8796–99]. There is increasing evidence about the diverse functions of these potassium channels in the regulation of mitochondrial matrix volume, ATP production and $Ca^{2+}$ homeostasis in mitochondria and essential factors determining the outcome of ischemic stress on cellular function and survival [Holmuhamedov E L, Jovanovic S, Dzeja P P, Jovanovic A, Terzic A. Mitochondrial ATP-sensitive $K^+$ channels modulate cardiac mitochondrial function. *Am J Physiol*. 1998;275:H1567–76; Garlid K D. Cation transport in mitochondria. *Biochim Biophys Acta*. 1996;1275:123–6; Halestrap A P. Regulation of mitochondrial metabolism through changes in matrix volume. *Biochem Soc Trans*. 1994;22:522–9; and Szewczyk A, Czyz A, Wojcik G, Wojczak L, Nalecz M. ATP-regulated $H^+$ channel in mitochondria: pharmacology and function. *J Bioenerg Biomembr*. 1996;28:147–52]. In fact several potassium channel openers can mimic ischemic preconditioning (IPC) in the heart, [Gross G J, Fryer R. Sarcolemmal versus mitochondrial ATP-sensitive K+ channels and myocardial preconditioning. *Circ Res*. 1999;973–79] and mitochondrial ATP-sensitive potassium channels are certainly involved in mediating these effects [Liu Y, Sato T, O'Rourke B, Marban E. Mitochondrial ATP-dependent potassium channels: novel effectors of cardioprotection? *Circulation*. 1998;97:2463–9; Garlid K D, Paucek P, Yarov-Yarovoy V, Murray H N, Darbenzio R B, D'Alonzo A J, Lodge N J, Smith M A, Grover G J. Cardioprotective effect of diazoxide and its interaction with mitochondrial ATP-sensitive K+ channels: possible mechanism of cardioprotection. *Circ Res*. 1997;81:1072–82; and, Baines C P, Liu G S, Birincioglu M, Critz S D, Cohen M V, Downey J M. Ischemic preconditioning depends on interaction between mitochondrial $K_{ATP}$ channels and actin cytoskeleton. *Am J Physiol*. 1999;276:H1361–68]. However, no study to date has investigated the possible beneficial role of mitochondrial ATP-sensitive potassium channel activation in vivo in the brain and the cerebral circulation.

EXAMPLE 1

Materials and Methods

Animals

Newborn piglets of either sex (1–7 days old, body weight 1–2 kg) were used. All procedures were approved by the Wake Forest University School of Medicine Institution Animal Care and Use Committee. The animals were anesthetized with sodium thiopental (30–40 mg/kg ip) followed by intravenous injection of α-chloralose (75 mg/kg). Supplemental doses of α-chloralose were given to maintain a stable level of anesthesia. The right femoral artery and vein were catheterized to record blood pressure and to administer drugs and fluids, respectively. The piglets were intubated via tracheotomy, and artificially ventilated with room air. The ventilation rate (~20/minutes) and tidal volume (~20 ml) were adjusted to maintain arterial blood gas values and pH in the physiological range. Body temperature was maintained at 37°–38° C. by a water-circulating heating pad. Body temperature, arterial pH and blood gases were also in the normal ranges, and did not vary significantly among different groups. For instance, in Group 5, the values were as follows: body temperature: 37.9±0.2° C.; pH: 7.51±0.03; $pCO_2$: 33.3±1.9 mmHg; $pO_2$: 97±4 mmHg.

Surgical Preparation

The head of the piglet was fixed in a stereotactic frame. The scalp was incised, and removed along with the connective tissue over the calvaria. A circular craniotomy (19 mm in diameter) was made in the left parietal bone. The dura was cut, and reflected over the skull. A stainless steel cranial window with three needle ports was placed into the craniotomy, sealed with bone wax, and cemented with cyanoacrylate ester (Super Glue, Japan) and dental acrylic.

The closed window was filled with artificial cerebrospinal fluid warmed to 37° C., and equilibrated with 6% $O_2$ and 6.5% $CO_2$ in balance $N_2$ to produce the following: pH=7.33, $pCO_2$=46 mmHg, and $pO_2$=43 mmHg. The artificial cerebrospinal fluid consisted of (mmol/L): NaCl 132, KCl 2.9, $CaCl_2$ 1.2, $MgCl_2$ 1.4, $NaHCO_3$ 24.6, urea 6.7, and glucose 3.7. Diameters of pial arterioles were measured using a microscope (Wild M36, Switzerland) equipped with a video camera (Panasonic, Japan) and a video micro scaler (IV-550, For-A-Co. Newton, Mass., USA). Following surgery, the cranial window was gently perfused with artificial cerebrospinal fluid until a stable baseline was obtained. At the conclusion of the experiments, the animals were killed while anesthetized with an intravenous bolus of KCl.

Drugs

The drugs used in this study were NMDA (Sigma), diazoxide (Sigma), 5-HD (H135, Research Biochemicals International), and aprikalim (Rhono-Roulenc-Rohourer).

Cerebral Ischemia

To induce global cerebral ischemia, a 3 mm hole was made by an electric drill with a toothless bit, and the dura was exposed. A hollow brass bolt was inserted in the left frontal cranium rostral to the cranial window, and secured in place with cyanoacrylate ester and dental acrylic. Cerebral ischemia was produced by infusion of artificial cerebrospinal fluid to raise intracranial pressure above arterial pressure. Ischemia was verified by the cessation of blood flow in the observed vessels. Previously, the inventor and others have shown using microspheres that cerebral blood flow is virtually zero in all brain areas examined during the ischemic period [Beasley T C, Bari F, Thore C, Thourikawala N, Louis T M, Busija D W. Cerebral ischemia/reperfusion increases endothelial nitric oxide synthase levels by an indomethacin-sensitive mechanism. *J Cereb Blood Flow Metab*. 1998;18:88–96]. Venous blood was withdrawn as necessary to maintain mean arterial blood pressure near normal values. At the conclusion of the ischemic period, the infusion tube was clamped, and the intracranial pressure returned to pre-ischemic values. The heparinized blood was reinfused intravenously.

Experimental Design

After obtaining stable baseline arteriolar diameters, the responses of cerebral arterioles to NMDA (10, 50, 100 μmol/L, except in Group 7) were examined. NMDA and all other drugs were dissolved in artificial cerebrospinal fluid, and administered topically through the injectable ports of the cranial window onto the brain surface with a single application. Arteriolar diameters were measured continuously for 5–7 minutes for each dose of NMDA. Next, the window was flushed with artificial cerebrospinal fluid, and the arteriolar diameters returned to baseline values.

Instrumented piglets (n=49) were then divided into 7 groups:

Group 1 (n=4): To assess if diazoxide has a direct effect on NMDA induced vasodilation. In the first group, the animals were treated with 10 μmol/L diazoxide for 10 minutes, but did not undergo ischemia. NMDA challenge was repeated 1 hour after treatment with diazoxide.

Group 2 (n=8): To repeat earlier findings on attenuation of NMDA-induced vasodilation by ischemia/reperfusion, the piglets in this group received vehicle artificial cerebrospinal fluid, and were exposed to 10 minutes of global cerebral ischemia followed by reperfusion. In all ischemia groups, NMDA-induced changes in pial arteriolar diameters were reexamined after the first hour of reperfusion. It has been shown that attenuation of cerebral vasodilation to NMDA is greatest 1 hour after ischemia/reperfusion (1 hour is also the shortest time after ischemia/reperfusion where the measurements are technically feasible).

Groups 3–5 (n=8, 8, and 12, respectively): To investigate the effect of diazoxide on the preservation of NMDA-induced vasodilation, piglets in these groups were pretreated with 1, 5, and 10 μmol/L diazoxide, respectively, for 10 minutes before the initiation of 10 minutes of global cerebral ischemia. The diazoxide was removed by flushing the window with artificial cerebrospinal fluid just before the initiation of ischemia.

Group 6 (n=5): To investigate the inhibitory effect of 5-HD on ATP-sensitive potassium channels activated by diazoxide, the piglets were pretreated with 100 μmol/L 5-HD for 5 minutes followed by co-application of 100 μmol/L 5-HD and 10 μmol/L diazoxide for 10 minutes before 10 minutes of ischemia. The diazoxide and 5-HD were removed by flushing the window with artificial cerebrospinal fluid just before the initiation of ischemia.

Group 7 (n=4): To study the effect of 5-HD on the sarcolemmal ATP-sensitive potassium channels, and the vascular response to NMDA, we examined the cerebral arteriolar responses to the non-selective $K_{ATP}$ channel opener aprikalim (10 μmol/L) followed by 100 μmol/L NMDA. Next, 10 μmol/L aprikalim and 100 μmol/L 5-HD were co applied for 10 minutes. The NMDA challenge was repeated 1 hour after the pretreatment with 5-HD and aprikalim. Previously, the inventor had shown that aprikalim treatment does not affect the vascular response to NMDA [Veltkamp R, Domoki F, Bari F, Busija D W. Potassium channel activators protect the N-methyl-D-aspartate-induced cerebral vascular dilation after combined hypoxia and ischemia in piglets. *Stroke*. 1998;29:837–43]. Between each drug application, the window was flushed several times with artificial cerebrospinal fluid until arteriolar diameters returned to baseline values.

Statistical Analysis

Data are expressed as mean±standard error of the mean (SEM). Pial arteriolar diameter data were analyzed using repeated measures analysis of variance. Pairwise comparisons were made using the Student-Newman-Keuls test where appropriate. Percent preservations of preischemic vasodilation data were analyzed with one-tailed t-test. P values <0.05 were considered statistically significant.

Results

Arterial blood pressure was in the normal range, and was not significantly different before and 1 hour after ischemia. For example, in Group 5, arterial pressure was 70±4 mmHg before ischemia, and 68±4 mmHg after ischemia/reperfusion (n=12).

Figure 2:
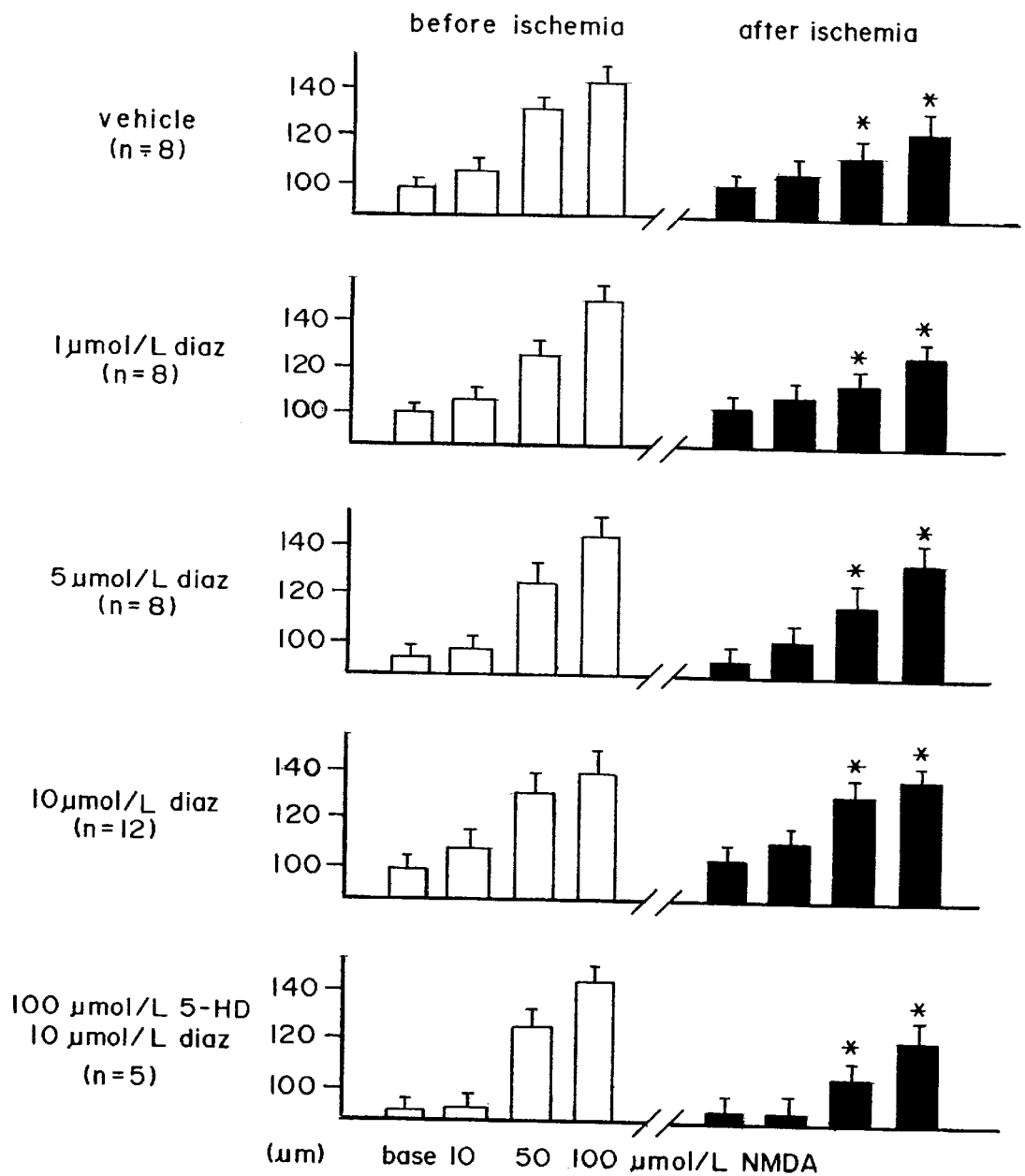
FIG. 2 illustrates the changes in pial arteriolar diameters in response to NMDA 1 hour after 10 minutes of cerebral ischemia. Baseline diameters (base) did not change significantly in any groups after ischemia/reperfusion. However, in the non-treated animals, arteriolar responses to 50 and 100 $\mu$mol/L NMDA were severely reduced approximately by 50%. Pretreatment with 1 $\mu$mol/L diazoxide did not affect the reduction in NMDA-induced vascular dilation by ischemia/reperfusion. In contrast, pretreatment with 5 or 10 $\mu$mol/L diazoxide resulted in preserved vascular responses, although the changes in pial arteriolar diameters were not significantly different (n.s.) compared to preischemic values. Co-application of 100 $\mu$mol/L 5-hydroxydecanoic acid (5-HD), a relatively specific inhibitor of mitochondrial ATP-sensitive potassium channel (mitoK$_{ATP}$), with 10 $\mu$mol/L diazoxide attenuates the protective effect of diazoxide. * denotes values that are significantly different from corresponding preischemic values, p<0,05.

Topical application of diazoxide did not affect pial vascular diameters significantly. Typically, there was only a transient dilation immediately upon application of diazoxide. Percent changes from baseline diameters were noted as follows: in Group 3, no vasoactivity was observed; in Group 4, 2±1%, in Group 5, 9±3%, but vascular diameters quickly returned to baseline values in 2–3 minutes. None of these changes were significantly different from the baseline values. As shown in FIGS. 1 and 2, NMDA elicited dose-dependent pial arteriolar vasodilation. In Group 1, 10 µmol/L diazoxide did not potentiate or attenuate vascular dilations to NMDA 1 hour after diazoxide treatment (see FIG. 1). FIG. 1 illustrates the effects of 10 µmol/L diazoxide on pial arteriolar responses to N-methyl-D-aspartate (NMDA). NMDA induced dose-dependent vasodilation that was unaffected 1 hour after topical application of diazoxide for 10 minutes (n=4). base: baseline diameter; *significantly different from corresponding baseline values, $p<0.05$.

Baseline arteriolar diameters were 100±2 µm before and 100±6 µm 1 hour after diazoxide treatment. Percent changes in pial arteriolar diameter from baseline to 10, 50, and 100 µmol/L NMDA (before versus 1 hour after diazoxide treatment) were, respectively: 3±1% versus 4±1%, 28±7% versus 26±9%, and 50±8% versus 47±8%.

Global cerebral ischemia (10 minutes) followed by reperfusion significantly reduced pial arteriolar responses to NMDA as shown in FIG. 2. FIG. 2 illustrates the changes in pial arteriolar diameters in response to NMDA 1 hour after 10 minutes of cerebral ischemia. Baseline diameters (base) did not change significantly in any groups after ischemia/reperfusion. However, in the non-treated animals, arteriolar responses to 50 and 100 µmol/L NMDA were severely reduced approximately by 50%. Pretreatment with 1 µmol/L diazoxide did not affect the reduction in NMDA-induced vascular dilation by ischemia/reperfusion. In contrast, pretreatment with 5 or 10 µmol/L diazoxide resulted in preserved vascular responses, although the changes in pial arteriolar diameters were not significantly different (n.s.) compared to preischemic values. Co-application of 100 µmol/L 5-hydroxydecanoic acid (5-HD), a relatively specific inhibitor of mitochondrial ATP-sensitive potassium channel (mitoK$_{ATP}$), with 10 µmol/L diazoxide attenuates the protective effect of diazoxide. * denotes values that are significantly different from corresponding preischemic values, $p<0,05$.

In Group 2, baseline arteriolar diameters were 100±3 µm before and 103±4 µm 1 hour after ischemia. Percent changes in pial arteriolar diameter from baseline to 10, 50, and 100 µmol/L NMDA (before versus 1 hour after ischemia) were, respectively: 6±2% versus 2±1%, 28±5% versus 9±3%, and 38±5% versus 16±4%. Thus, vascular dilations to 100 µmol/L NMDA were diminished by 50% as shown in FIG. 3.

Figure 3:
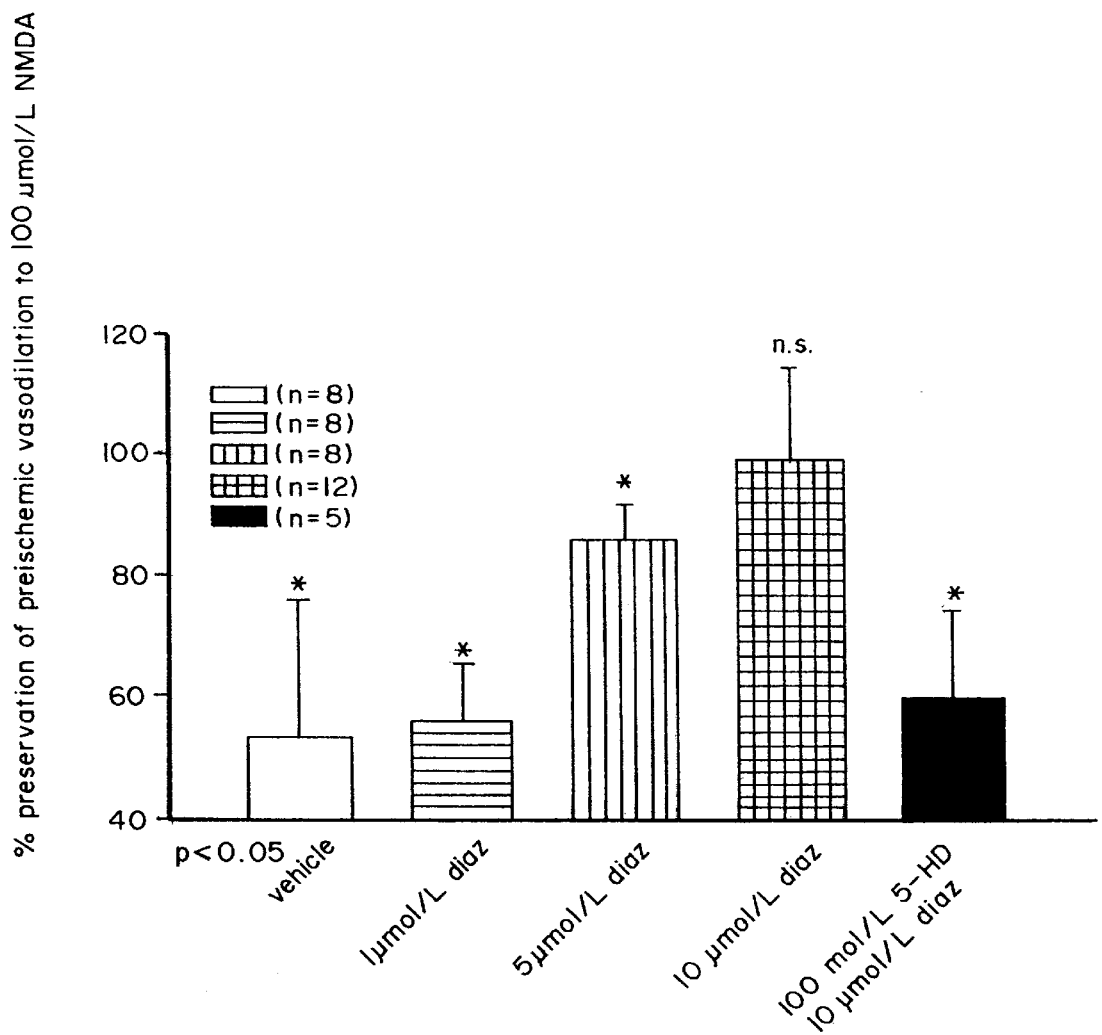
FIG. 3 illustrates the protective effect of diazoxide on 100 $\mu$mol/L NMDA-induced pial arteriolar dilation. Data are expressed as percent preservation of dilation compared to preischemic values. Note the dose-dependent preservation of vascular responses in the diazoxide treated groups. For example, at 10 $\mu$mol/L diazoxide, the vascular response was virtually identical to preischemic value. Also shown, 5-HD antagonizes the effect of diazoxide. n.s.:non significant, *denotes significantly different value from preischemic value.

FIG. 3 illustrates the protective effect of diazoxide on 100 µmol/L NMDA-induced pial arteriolar dilation. Data are expressed as percent preservation of dilation compared to preischemic values. Note the dose-dependent preservation of vascular responses in the diazoxide treated groups. For example, at 10 µmol/L diazoxide, the vascular response was virtually identical to preischemic value. Also shown, 5-HD antagonizes the effect of diazoxide. n.s.:non significant, *denotes significantly different value from preischemic value.

Diazoxide had a dose-dependent effect on preservation of NMDA-induced vasodilation following ischemia/reperfusion. In Group 3, decreases in pial arterial responsiveness to NMDA were similar to those observed in Group 2 (see FIGS. 2 and 3). In Group 3, baseline arteriolar diameters were 102±3µm before and 104±3 µm 1 hour after ischemia. Percent changes in pial arteriolar diameter from baseline to 10, 50, and 100 µmol/L NMDA (before versus 1 hour after ischemia) were, respectively: 5±2% versus 3±1%, 20±7% versus 8±2%, and 38±5% versus 19±3%. In contrast, in Groups 4–5, a dose-dependent preservation of pial vascular responses to NMDA was observed (FIGS. 2 and 3). More specifically, in Group 4, baseline arteriolar diameters were 95±3 µm before and 95±4 µm 1 hour after ischemia. Percent changes in the pial arteriolar diameter from baseline to 10, 50, and 100 µmol/L NMDA (before versus 1 hour after ischemia) were calculated as follows: 4±0% versus 7±2%, 30±10% versus 23±6%, and 45±6% versus 37±3% In Group 5, baseline arteriolar diameters were 102±6 µm before and 106±5 µm 1 hour after ischemia. Percent changes in pial arteriolar diameter from baseline to 10, 50, and 100 µmol/L NMDA (before versus 1 hour after ischemia) were as follows, respectively: 7±1% versus 6±2%, 28±5% versus 24±4%, and 36±5% versus 32±4%. In view of the foregoing, pretreatment with 10 µmol/L diazoxide resulted in virtually full preservation of pial arteriolar responses to NMDA 1 hour after ischemia/reperfusion compared to pre-ischemic values.

Topical application of the ATP-sensitive potassium channel antagonist, 5-HD, and co-application of 5-HD with diazoxide did not alter pial arteriolar diameters. Also, 5-HD treatment did not affect pial arteriolar responses to NMDA. In Group 7, baseline arteriolar diameters were 105±9 µm before and 103±7 µm 1 hour after pretreatment with 5-HD. Percent changes in pial arteriolar diameter from baseline to 100 µmol/L NMDA were (before versus 1 hour after 5-HD treatment) 52±3% versus 56±7%. However, pretreatment with 5-HD and diazoxide abolished the protection on NMDA-induced vasodilation achieved by diazoxide alone (see FIGS. 2 and 3). In Group 6, baseline arteridar diameters were 90±6 µm before and 92±6 µm 1 hour after ischemia. Percent changes in pial arteriolar diameter from baseline to 10, 50, and 100 µmol/L NMDA (before versus 1 hour after ischemia) were, respectively: 3±1% versus 0±0%, 40±12% versus 19±6%, and 61±7% versus 33±5%. Interestingly, co application of 5-HD with aprikalim did not block the vasodilation elicited by aprikalim. In Group 7, pial baseline arteriolar diameters were 102±8 µm before application of aprikalim alone, and 101±7 µM before co-application of aprikalim and 5-HD. Percent changes in pial arteriolar diameter from baseline to 10 µmol/L aprikalim were (aprikalim alone versus aprikalim+5-HD) 65±6% versus 65±6%.

Based on the foregoing studies, the selective mitochondrial ATP-sensitive potassium channel opener, diazoxide, dose dependently preserves NMDA-induced cerebral arteriolar vasodilation after ischemia/reperfusion in piglets. Since NMDA-induced vasodilation is dependent upon intact neuronal function, evidence is presented for the first time showing an in vivo protective effect of diazoxide after ischemia/reperfusion in the central nervous system.

Previously, the inventor found that the non-selective K$_{ATP}$ opener, aprikalim, protected NMDA-induced vasodilation after combined hypoxia-ischemia (H/I) [Veltkamp R, Domoki F, Bari F, Busija D W. Potassium channel activators protect the N-methyl-D-aspartate-induced cerebral vascular dilation after combined hypoxia and ischemia in piglets. *Stroke*. 1998;29:837–43]. The protective effect of aprikalim was shown to be mediated by neuronal rather than vascular non-selective K$_{ATP}$ channel openers, and was independent of the vasodilation elicited by aprikalim. Data from the present studies confirm that the protective effect of pretreatment with potassium channel openers is independent of vasodilation accompanied by the administration of such drugs. Diazoxide showed no significant vasoactivity, but preserved NMDA-induced dilation. The beneficial effects of ATP-sensitive potassium channel openers in reducing injury by ischemia/reperfusion have been most extensively studied in the heart. These potassium channel openers serve as the final common pathway in the event of ischemic preconditioning (IPC), a phenomenon where short periods of ischemia protect the heart from subsequent exposure of a more prolonged period of ischemia. Potassium channel openers mimic IPC, [Gross G J, Fryer R. Sarcolemmal versus mitochondrial ATP-sensitive K+ channels and myocardial preconditioning. *Circ Res*. 1999;973–79; Liu Y, Sato T, O'Rourke B, Marban E. Mitochondrial ATP-dependent potassium channels: novel effectors of cardioprotection? *Circulation*. 1998;97:2463–9; Garlid K D, Paucek P, Yarov-Yarovoy V, Murray H N, Darbenzio R B, D'Alonzo A J, Lodge N J, Smith M A, Grover G J. Cardioprotective effect of diazoxide and its interaction with mitochondrial ATP-sensitive K+ channels: possible mechanism of cardioprotection. *Circ Res*. 1997;81:1072–82; and Baines C P, Liu G S, Birincioglu M, Critz S D, Cohen M V, Downey J M. Ischemic preconditioning depends on interaction between mitochondrial $K_{ATP}$ channels and actin cytoskeleton. *Am J Physiol*. 1999;276:H1361–68], and the protection by IPC is blocked by ATP-sensitive potassium channel inhibitors [Auchampach J, Grover G, Gross G. Blockade of ischemic preconditioning in dogs by the novel ATP-dependent potassium channel antagonist sodium 5-hydroxydecanoate. *Cardiovasc Res*. 1992;26:1054–62; Gross G, Auchampach J. Blockade of the ATP-sensitive potassium channels prevents myocardial preconditioning. *Circ Res*. 1992;70:223–33; and Schulz R, Rose J, Heusch G. Involvement of activation of ATP-dependent potassium channels in ischemic preconditioning in swine. *Am J Physiol*. 1994;267:H1341–52]. The exact mechanism of this remarkable effect has not yet been elucidated.

The discovery of mitochondrial ATP-sensitive potassium channels added further complexity to the interpretation of experimental data from pharmacological interventions on these channels. Unfortunately, there are no absolutely selective pharmacological tools to assess these channels in vivo. However, a consistent and unique feature of these channels is their remarkably selective sensitivity to opening by diazoxide. The mitochondrial ATP-sensitive potassium channel was found to be more than 2000-fold more sensitive to diazoxide than the sarcolemmal ATP-sensitive potassium channel in bovine cardiac myocytes ($K_{1/2}$ was 0.4 $\mu$mol/L for the mitochondrial ATP-sensitive potassium channel versus 855 $\mu$mol/L for the sarcolemmal potassium channel). In contrast, cromakalim was equally potent opener of both mitochondrial and plasma membrane [Garlid K D, Paucek P, Yarov-Yarovoy V, Xiaocheng Sun, Schindler P A. The mitochondrial $K_{ATP}$ channel as a receptor for potassium channel openers. *J Biol Chem*. 1996;271:8796–99]. Subsequently, mitochondrial ATP-sensitive potassium channels selective concentrations (5–20 $\mu$mol/L) of diazoxide have been demonstrated to improve functional recovery in isolated rat hearts after ischemia/reperfusion in a similar manner to a non-selective potassium channel opener, cromakalim. The cardioprotection by diazoxide was inhibited by ATP-sensitive potassium channels inhibitors, glibenclamide and 5-HD, confirming the effect of diazoxide via the ATP-sensitive potassium channels [Garlid K D, Paucek P, Yarov-Yarovoy V, Murray H N, Darbenzio R B, D'Alonzo A J, Lodge N J, Smith M A, Grover G J. Cardioprotective effect of diazoxide and its interaction with mitochondrial ATP-sensitive K+ channels: possible mechanism of cardioprotection. *Circ Res*. 1997;81:1072–82]. In a different study involving intact rabbit ventricular myocytes, diazoxide induced mitochondrial depolarization as demonstrated by flavoprotein fluorescence with a $K_{1/2}$ of 27 $\mu$mol/L, but did not affect the simultaneously measured sarcolemmal ATP-sensitive potassium channel current [Liu Y, Sato T, O'Rourke B, Marban E. Mitochondrial ATP-dependent potassium channels: novel effectors of cardioprotection? *Circulation*. 1998;97:2463–9]. These findings strongly suggest the involvement of mitochondrial ATP-sensitive potassium channels in the development of acute and perhaps delayed IPC in the heart.

In the present invention, we used topical diazoxide (1–10 $\mu$mol/L) in the mitochondrial ATP-sensitive potassium channel selective dose range. A good indication of selective activation could be shown by the absence of significant vasodilation accompanied by application of diazoxide. The vasodilatory effect of potassium channel openers on cerebral arterioles is directly mediated by the sarcolemmal potassium channels. Administration of 5–10 $\mu$mol/L diazoxide elicited only 2–9% arteriolar dilation, and the response was transient, (i.e., did not last for more than 1–2 minutes). In contrast, it was discovered that the non-selective ATP-sensitive potassium channel opener, aprikalim, (10 $\mu$mol/L) elicits ~60–70% increases in vascular diameters, and the vasodilation does not wane. Moreover, the dose-dependent effect of diazoxide on preservation of the NMDA-induced vasodilation after ischemia/reperfusion was inhibited by a selective $K_{ATP}$ antagonist 5-HD, and 5-HD was found to be selective for mito$K_{ATP}$ channels at least in some experimental designs [Liu Y, Sato T, O'Rourke B, Marban E. Mitochondrial ATP-dependent potassium channels: novel effectors of cardioprotection? *Circulation*. 1998;97:2463–9; Garlid K D, Paucek P, Yarov-Yarovoy V, Murray H N, Darbenzio R B, D'Alonzo A J, Lodge N J, Smith M A, Grover G J. Cardioprotective effect of diazoxide and its interaction with mitochondrial ATP-sensitive K+ channels: possible mechanism of cardioprotection. *Circ Res*. 1997;81:1072–82; and Sato T, O'Rourke B, Marban E. Modulation of mitochondrial ATP-dependent $K^+$ channels by protein kinase C. *Circ Res*. 1998;83:110–4]. Also, in the present experimental model, 5-HD did not inhibit the vasodilation induced by aprikalim suggesting minutes or effects on plasmolemmal ATP-sensitive potassium channels. Based on these observations, one can reasonably conclude that the protective effect of diazoxide on neuronal-vascular function after ischemia/reperfusion is most probably mediated by activation of the mitochondrial ATP-sensitive potassium channels.

The mechanism by which activation of the mitochondrial ATP-sensitive potassium channels may lead to increased resistance to ischemia/reperfusion remains to be clarified. In the present experimental model, NMDA-induced vascular response is severely attenuated at 1 hour after ischemia/reperfusion, and responsiveness gradually returns over the time course of 2–4 hours [Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30 and Veltkamp R, Domoki F, Bari F, Louis T M, Busija D W. Inhibitors of protein synthesis preserve the N-methyl-D-aspartate-induced cerebral arteriolar dilation after ischemia in piglets. *Stroke*. 1999;30:148–52]. Although the duration of global cerebral ischemia (10 minutes) used in the present study has been thought to cause only reversible mitochondrial alterations, mitochondria have been shown to recover full function in 1–2 hours after reperfusion [Echncrona S, Mela L, Siesjo B K. Recovery of brain mitochondrial function in the rat after complete and incomplete cerebral ischemia. *Stroke*. 1979;10:437–46 and Sims N R. Selective impairment of respiration in mitochondria isolated from brain subregions following transient forebrain ischemia in the rat. *J Neurochem*. 1991;56:1836–44]. Thus, the attenuation of the NMDA-mediated cerebral arteriolar response is not likely due to energy failure by inhibited mitochondrial function. This view is further supported by our earlier findings that kainate-induced vasodilation is resistant to ischemia in the same experimental model [Bari F, Louis T M, Busija D W. Kainate-induced cerebrovascular dilation is resistant to ischemia in piglets. *Stroke*. 1997;28:1272–6]. Also, neuronal nitric oxide synthase levels and activity are unchanged by ischemia/reperfusion, and cerebral arterioles show normal responses to exogenous nitric oxide donors like sodium nitroprusside after ischemia [Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30 and Veltkamp R, Domoki F, Bari F, Busija D W. Potassium channel activators protect the N-methyl-D-aspartate-induced cerebral vascular dilation after combined hypoxia and ischemia in piglets. *Stroke*. 1998;29:837–43]. Therefore, the primary target of ischemia/reperfusion may be the NMDA-receptor itself. The acute effect of ischemia on NMDA-induced pial arteriolar vasodilation has been amply demonstrated to be mediated by reactive oxygen species (see FIG. 4).

Figure 4:
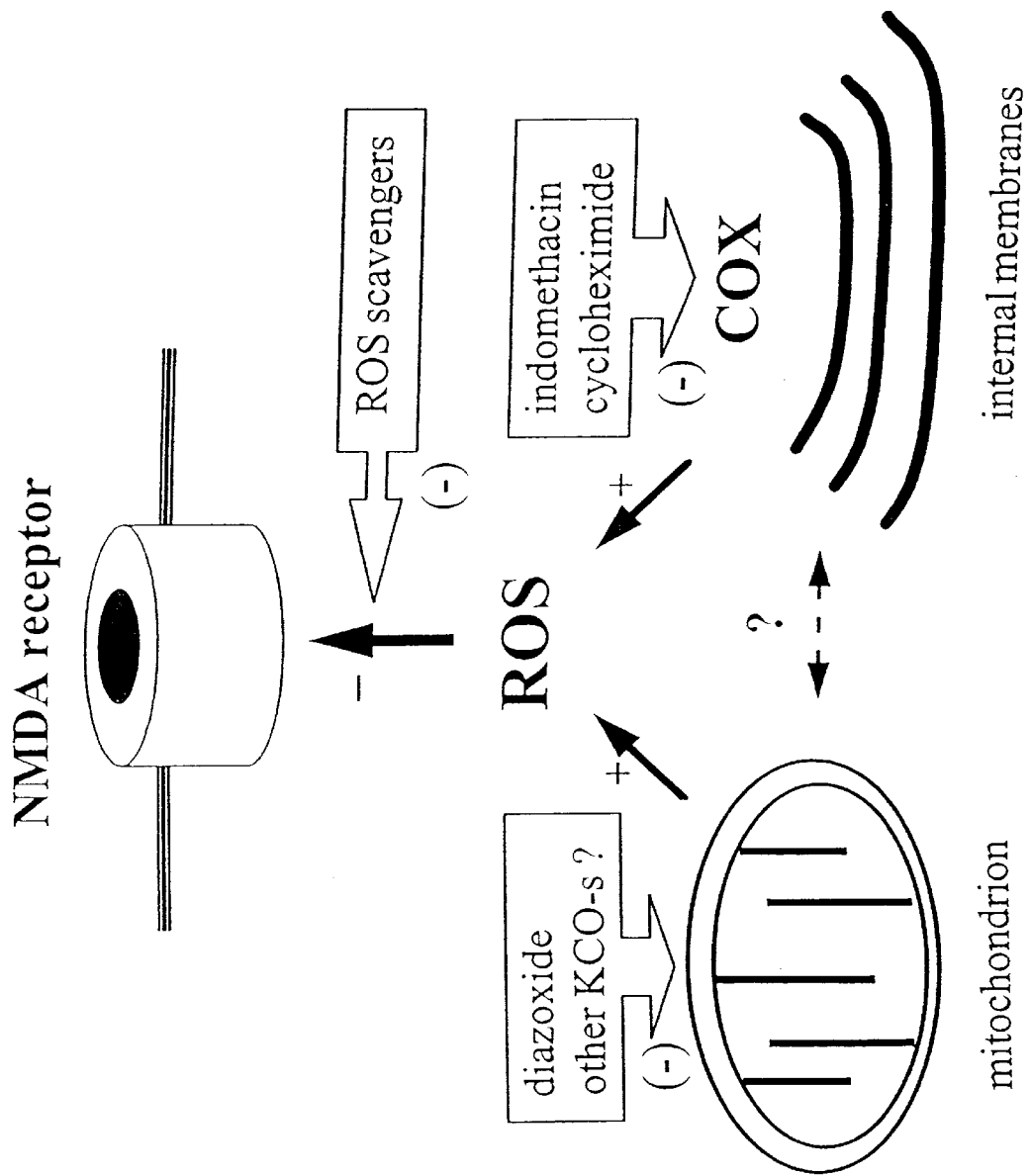
FIG. 4 illustrates the preservation of NMDA-induced cerebral vasodilation after ischemia/reperfusion. The most sensitive component of this neurono-vascular sequence to ischemia/reperfusion may be the NMDA-receptor itself. Reactive oxygen species (ROS) produced by mitochondria and cyclooxygenase (COX) seem to play a pivotal role in attenuating the NMDA-induced vasodilation. Thus, pretreatment with ROS scavengers, COX inhibitor indomethacin, or protein (including COX) synthesis inhibitor, cycloheximide, just prior to ischemia/reperfusion results in preserved vascular responsiveness to NMDA. NMDA-induced dilation is also preserved by pretreatment with diazoxide, a selective mitoK$_{ATP}$ opener and other potassium channel openers (KCO). Activation of mitoK$_{ATP}$ may reduce generation of reactive oxygen species in the reperfusion. Reduction in either COX-derived or mitochondrial reactive oxygen species production may be sufficient to preserve the vascular response to NMDA after ischemia/reperfusion. However, a potentiating interaction between these sources of reactive oxygen species is conceivable, but unknown.

FIG. 4 illustrates the preservation of NMDA-induced cerebral vasodilation after ischemia/reperfusion. The most sensitive component of this neurono-vascular sequence to ischemia/reperfusion may be the NMDA-receptor itself. Reactive oxygen species (ROS) produced by mitochondria and cyclooxygenase (COX) seem to play a pivotal role in attenuating the NMDA-induced vasodilation. Thus, pretreatment with ROS scavengers, COX inhibitor indomethacin, or protein (including COX) synthesis inhibitor, cycloheximide, just prior to ischemia/reperfusion results in preserved vascular responsiveness to NMDA. NMDA-induced dilation is also preserved by pretreatment with diazoxide, a selective mitoK$_{ATP}$ opener and other potassium channel openers (KCO). Activation of mitoK$_{ATP}$ may reduce generation of reactive oxygen species in the reperfusion. Reduction in either COX-derived or mitochondrial reactive oxygen species production may be sufficient to preserve the vascular response to NMDA after ischemia/reperfusion. However, a potentiating interaction between these sources of reactive oxygen species is conceivable, but unknown.

Thus, NMDA-induced vascular response has been found to be preserved by reactive oxygen species scavengers, and inhibitors of cyclooxygenase activity, [Bari F, Errico R A, Louis T M, Busija D W. Differential effects of short-term hypoxia and hypercapnia on N-methyl-D-aspartate-induced cerebral vasodilatation in piglets. *Stroke*. 1996;27:1634–39; Busija D W, Meng W, Bari F, McGough P S, Errico R A, Tobin J R, Louis T M. Effects of ischemia on cerebrovascular responses to N-methyl-D-aspartate in piglets. *Am J Physiol*. 1996;270:H1225–30; Pourcyrous M, Leffler C W, Bada H S, Korones S B, Busija D W. Brain superoxide anion generation in asphyxiated piglets and the effect of indomethacin at therapeutic dose. *Pediatr Res*. 1993;34:366–369; and Veltkamp R, Domoki F, Bari F, Louis T M, Busija D W. Inhibitors of protein synthesis preserve the N-methyl-D-aspartate-induced cerebral arteriolar dilation after ischemia in piglets. *Stroke*. 1999;30:148–52], a major source of reactive oxygen species after ischemia/reperfusion [Armstead W M, Mirro R, Busija D W, Leffler C W. Postischemic generation of superoxide anion by newborn pig brain. *Am J Physiol*. 1988;255:H401–3]. Our recent observations on the preservation of neural function with potassium channel openers after H/I were somewhat difficult to reconcile with the general scheme of the pathomechanism of the effect of ischemia/reperfusion on NMDA induced neurono-vascular sequence. However, the present results may indeed link the beneficial effect of potassium channel openers on the preservation of NMDA-induced vasodilation to reducing oxidative stress on the neurons involved in this response. We further hypothesize that activation of mitochondrial ATP-sensitive potassium channels by potassium channel openers may reduce mitochondrial reactive oxygen species production.

Currently, the physiological role of mitochondrial ATP-sensitive potassium channels is still debated and mostly speculative. Briefly, these potassium channels seem to control the activity of the electron transport chain via regulating mitochondrial matrix volume by regulated $K^+$ uptake. The physiological pattern of activation and inhibition of these channels are largely unknown, but ironically, the physiological role of ATP as a regulator is unlikely [Paucek P, Yarov-Yarovoy V, Xiaocheng S, Garlid K D. Inhibition of the mitochondrial $K_{ATP}$ channel by long chain acyl-CoA esters and activation by guanine nucleotides. *J Biol Chem*. 1996;271:32084–8]. In isolated mitochondria, potassium channel openers induce slight swelling, partially dissipate the transmembrane potential (ÄØ, negative inside), but increase the activity of electron transport chain. Hence, the chemical proton gradient (ÄpH, alkaline inside) and, thus, the total the protonmotive hardly changes [Garlid K D, Paucek P, Yarov-Yarovoy V, Xiaocheng Sun, Schindler P A. The mitochondrial $K_{ATP}$ channel as a receptor for potassium channel openers. *J Biol Chem*. 1996;271:8796–99; Holmuhamedov E L, Jovanovic S, Dzeja P P, Jovanovic A, Terzic A. Mitochondrial ATP-sensitive $K^+$ channels modulate cardiac mitochondrial function. *Am J Physiol*. 1998;275:H1567–76; Garlid K D. Cation transport in mitochondria. *Biochim Biophys Acta*. 1996;1275:123–6; Halestrap A P. Regulation of mitochondrial metabolism through changes in matrix volume. *Biochem Soc Trans*. 1994;22:522–9; and Szewczyk A, Czyz A, Wojcik G, Wojczak L, Nalecz M. ATP-regulated $K^+$ channel in mitochondria: pharmacology and function. *J Bioenerg Biomembr*. 1996;28:147–52]. However, the activity of numerous important transport mechanisms depends either on ÄØ or ÄpH.

One such possibly crucial "metabolite" may be $Ca^{2+}$. Mitochondria readily uptake $Ca^{2+}$ when intracellular levels increase above a so-called mitochondrial "buffer" concentration. $Ca^{2+}$ is transported through the mitochondrial inner membrane via the electrogenic $Ca^{2+}$ uniporter down its electrochemical gradient, thus the rate of this transport is dependent upon ÄØ [Gunter T E, Gunter K K, Sheu S-S, Gavin C E. Mitochondrial calcium transport: physiological and pathological relevance. *Am J Physiol*. 1994;267:C313–39]. Mitochondrial $Ca^{2+}$ overload substantially influences the recovery of mitochondrial function following ischemic stress. For example, increased mitochondrial $Ca^{2+}$ sequestration has been demonstrated to increase production of reactive oxygen species [Dugan L L, Sensi S L, Canzoniero L M T, Handran S D, Rothman S M, Lin T-S, Goldberg M P, Choi D W. Mitochondrial production of reactive oxygen species in cortical neurons following exposure to N-methyl-D-aspartate. *J Neurosci*. 1995;15:6377–88 and Dykens J A. Isolated cerebral and cerebellar mitochondria produce free radicals when exposed to elevated $Ca^{2+}$ and $Na^+$: implications for neurodegeneration. *J Neurochem.* 1994;63:584–91]. Opening of mitochondrial ATP-sensitive potassium channels should decrease mitochondrial $Ca^{2+}$ uptake by decreasing $\bar{A}\emptyset$, and in fact, potassium channel openers induce release of $Ca^{2+}$ from $Ca^{2+}$-preloaded mitochondria in vitro [Holmuhamedov E L, Jovanovic S, Dzeja P P, Jovanovic A, Terzic A. Mitochondrial ATP-sensitive $K^+$ channels modulate cardiac mitochondrial function. *Am J Physiol.* 1998;275:H1567–76].

In summary, diazoxide in a mitochondrial ATP-sensitive potassium channel-selective range dose dependently preserves neuronal function as demonstrated by NMDA-induced arteriolar dilation after ischemia/reperfusion. The acute effect of these mitochondrial potassium channel openers may be mediated by decreasing mitochondrial reactive oxygen species production in the immediate reperfusion. This effect may be important in the protective effect of other non-specific potassium channel openers as well. This finding may well be the basis for the development of new therapies to reduce neuronal injury after global hypoxic-ischemic stress in the newborn.

The present invention firther contemplates the use of diazoxide or any derivative, analog, or metabolite thereof for use as a neuroprotective therapeutic agent to preserve tissues and organs which are being used for transplantation or reattachment purposes. Diazoxide may be admrinistered into the tissue or organ prior to removal, and would protect the tissue or organ against cellular injury and death during removal, storage, transplantation, or reattachment. The following example serves only to illustrate the protocol for performing this methodology, and in no way is to be construed as limiting the scope of the present invention.

EXAMPLE 2

Protocol to Study the Effects of Diazoxide Treatment on Survival of Transplanted Cells The protocol described by Mehta et al. will be used to study the effects of diazoxide treatment on the survival of transplanted cells (Mehta, V., M. Hong, J. Spears, and 1. Mendez. Enhancement of graft survival and sensorimotor behavioral recovery in rats undergoing transplantation with dopaminergic cells exposed to glial cell line—derived neurotrophic factor. *Journal of Neurosurgery* 88:1088–1095, 1998). The objective of the study is to test the hypothesis that diazoxide treatment of brain grafts will enhance survival of cells when they are transplanted into the brains of recipient animals.

In order to simulate the Parkinson's Disease model described by Mehta et al., anesthetized adult rats will receive two stereotaxic injections of a total of 3.6 $\mu$g of 6-hydroxydopamine (6-OHDA) into the right nigrostriatal dopaminergic pathway. The injections are via microsyringes into two locations of the nigrostriatal dopaminergic pathway over a period of several minutes. Stereotaxic coordinates are −4.4 anteroposterior, 1.2 lateral, 7.8 ventral, and −2.4 tooth bar/−4.0 anteroposterior, 0.8 lateral, 8 ventral, and 3.4 tooth bar. After a 2 week recovery period, the animals will be tested via an amphetamine challenge (5 mg/kg, i.p.). If the animals exhibit 480 or more ipsilateral rotations/hour, then they will be included in the study.

Ventral mesencephalic tissue will be harvested from 14-day old rat fetuses. The tissue will be stored at 4° C. for 6 days in a phosphate buffered, calcium-free hibernation medium. The tissue will be divided into 5 groups and treated as follows: 1) stored in the buffer alone; 2) stored in buffer with 1 $\mu$mol/Liter of diazoxide; 3) stored in buffer with 5 $\mu$mol/Liter of diazoxide; 4) stored in buffer with 10 $\mu$mol/ Liter of diazoxide; and 5) stored in buffer with 10 $\mu$mol/Liter of diazoxide plus 100 $\mu$mol/Liter of 5-hydroxydecanoic acid (5-HD) (an inhibitor of mitochondrial ATP-sensitive potassium channels).

Using the micro grafting technique described by Nikkah et al., 600,000 cells will be implanted into the striatum (Nikkhah G., J. Eberhard, M. Olsson, and A. Bjorklund. Preservation of fetal ventral mesencephalic cells by cool storage: in-vitro viability and TH-positive neuron survival after micro transplantation to the striatum. *Brain Research* 687: 22–34, 1990; and Nikkhah G., M. Olsson, J. Eberhard, C. Bentlage, M. G. Cunningham, and A. Bjorklund. A micro transplantation approach for cell suspension grafting in the rat Parkinson model: a detailed account of the methodology. *Neuroscience* 63:57–72, 1994). At 8 weeks after transplantation, the animals are killed with an overdose of anesthesia, and the brains are perfused fixed with formalin, frozen, and coronally sectioned at 40 $\mu$m.

Sections are immunostained for tyrosine hydroxylase (TH) using traditional methods. TH-immunopositive neurons in the grafted striatum will be counted by using a 10×10 ocular lens grid by blinded observers on every fourth section. The final graft cell number is calculated by using Abercrombie's formula (Abercrombie, M. Estimation of nuclear population from microtome sections. *Anatomical Record* 94:239–247, 1946) wherein P=1f AM [D+M], where P is the corrected cell number, A is the raw cell count, D is the average cell diameter, M is the section thickness, and f is the frequency of selected sections. Data will be analyzed using analysis of variance. If a diazoxide treatment increases the number of TH-immunopositive cells on the lesioned side as is expected, one can conclude that activation of ATP-sensitive potassium channels prior to transplantation preserves cell viability, and prevents cell death of the transplanted cells.

All references referred to herein are hereby incorporated by reference in their entirety.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method for activating neuronal $K_{ATP}$ channels comprising delivering a sufficient amount of diazoxide (7-chloro-3-methyl-2H-1,2,4-benzo-thiadiazine 1,1-dioxide) to a channel site.

2. The method of claim 1 wherein the sufficient amount comprises a dosage ranging from 0.1 $\mu$M to 150 $\mu$M.

3. The method of claim 1 further comprising delivering a sufficient amount of aprikalim to the channel site.

4. The method of claim 3 wherein the amount of aprikalim comprises a dosage ranging from from 0.1 $\mu$M to 150 $\mu$M.

5. The method of claim 1 wherein the step of delivering comprises introducing the dosage of diazoxide into a mammals circulatory system.

6. A method for activating mitochondrial $K_{ATP}$ channels comprising delivering a sufficient amount of diazoxide (7-chloro-3-methyl-2H-1,2,4-benzo-thiadiazine 1,1-dioxide) to a mitochondrial site.

7. The method of claim 6 wherein the sufficient amount comprises a dosage ranging from 0.1 $\mu$M to 150 $\mu$M.

8. The method of claim 6 further comprising delivering a sufficient amount of aprikalim to the mitochondrial site.

9. The method of claim 8 wherein the amount of aprikalim comprises a dosage ranging from 0.1 µM to 150 µM.

10. The method of claim 6 wherein the step of delivering comprises introducing the dosage of diazoxide into a mammals circulatory system.

11. A method of protecting neuronal function in vivo in the brain and the cerebral circulation, comprising the step of administering to a mammal a therapeutically effective dosage of a $K_{ATP}$ channel opening composition prior to a medical procedure.

12. The method of claim 11 wherein the $K_{ATP}$ channel opening composition comprises diazoxide.

13. The method of claim 11 wherein the $K_{ATP}$ channel opening composition comprises aprikalim.

14. The method of claim 11 wherein the medical procedure comprises one or more of the following: cardiopulmonary bypass, carotid endarterectomy, cardiac catheterization, angioplasty and/or clipping of aneurysms.

15. The method of claim 11 wherein the therapeutically effective amount comprises a dosage ranging from 0.1 µM to 150 µM.

16. The method of claim 12 further comprising administering to the mammal a therapeutically effective amount of aprikalim prior to the scheduled medical or surgical procedure.

17. A method of protecting neuronal function in vivo in the brain and the cerebral circulation, comprising the step of administering to a mammal a therapeutically effective dosage of a $K_{ATP}$ channel opening composition following a neurological event.

18. The method of claim 17 wherein the $K_{ATP}$ channel opening composition comprises diazoxide.

19. The method of claim 17 wherein the $K_{ATP}$ channel opening composition comprises aprikalim.

20. The method of claim 17 wherein the administering occurs within 10 minutes of the event.

21. The method of claim 17 wherein the neurological event includes one or more of the following: stroke, general circulatory failure, seizures, apnea, and intracranial bleeding.

22. The method of claim 17 wherein the therapeutically effective amount comprises a dosage ranging from 0.1 µM to 150 µM.

23. The method of claim 18 further comprising administering to the mammal a therapeutically effective amount of aprikalim.

24. A method of protecting tissues and organs against cellular damage associated with transplantation or reattachment, comprising the step of infusing a therapeutic dosage of a $K_{ATP}$ channel opening composition into tissues or organs prior to the removal of the tissues or organs from a mammal.

25. The method of claim 24 wherein the $K_{ATP}$ channel opening composition comprises diazoxide.

26. The method of claim 24 wherein the $K_{ATP}$ channel opening composition comprises aprikalim.

27. The method of claim 24 wherein the therapeutic dosage comprises a dosage ranging from 0.1 µM to 150 µM.

28. The method of claim 24 further comprising infusing into the tissue or organ a therapeutically effective amount of aprikalim.

* * * * *